(12) United States Patent
Fukumoto

(10) Patent No.: US 10,072,038 B2
(45) Date of Patent: *Sep. 11, 2018

(54) CRYSTAL OF AMMONIUM N-ACETYLNEURAMINATE ANHYDRATE, AND PROCESS FOR PRODUCING SAME

(71) Applicant: KYOWA HAKKO BIO CO., LTD., Tokyo (JP)

(72) Inventor: Kazunari Fukumoto, Tokyo (JP)

(73) Assignee: KYOWA HAKKO BIO CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/545,881

(22) PCT Filed: Jan. 27, 2016

(86) PCT No.: PCT/JP2016/052311
§ 371 (c)(1),
(2) Date: Jul. 24, 2017

(87) PCT Pub. No.: WO2016/121810
PCT Pub. Date: Aug. 4, 2016

(65) Prior Publication Data
US 2018/0002364 A1    Jan. 4, 2018

(30) Foreign Application Priority Data

Jan. 28, 2015   (JP) .................................. 2015-014541

(51) Int. Cl.
C07H 5/06   (2006.01)

(52) U.S. Cl.
CPC ............ C07H 5/06 (2013.01); *C07B 2200/13* (2013.01)

(58) Field of Classification Search
None
See application file for complete search history.

(56) References Cited

U.S. PATENT DOCUMENTS 4,698,332 A   10/1987   Ogasawara et al.

FOREIGN PATENT DOCUMENTS

| JP | 61-68418 A | 4/1986 |
| JP | 63-028411 B2 | 6/1988 |
| WO | WO 2016/017677 A1 | 2/2016 |

OTHER PUBLICATIONS

Flippen et al., "The Crystal Structure of β-$_D$-N-Acetylneuraminic Acid Dihydrate (Sialic Acid), $C_{11}H_{19}NO_9 \cdot 2H_2O$," *Structural Crystallography and Chrystal Chemistry*, 29: 1881-1886 (1973).
Ogura et al., "Stereochemical Characterization of Hydrated and Dehydrated Crystals of N-Acetylneuraminic Acid as Revealed by the IR, CD, and $^{13}$C Cross Polarization-Magic Angle Spinning NMR Spectroscopy," *Chemistry Letters*, 13(6): 1003-1006 (1984).
Takahashi et al., "Total Synthesis of Neu5Ac via Alkylation of 2-Alkoxy-2-cyanoacetate with a Sugar-Derived Bromide," *Synlett*, 9: 1065-1066 (1997).
Takahashi et al., "Synthetic Studies of Sialo-glycoconjugates," *Symposium on the Chemistry of Natural Products, Symposium Papers*, 39: 49-54 (1997).
Japanese Patent Office, International Search Report in International Patent Application No. PCT/JP2016/052311 (Apr. 19, 2016).

*Primary Examiner* — Layla D Berry
(74) *Attorney, Agent, or Firm* — Leydig, Voit & Mayer, Ltd.

(57) ABSTRACT

According to the present invention, a crystal of ammonium N-acetylneuraminate anhydrate, and a process for producing a crystal of ammonium N-acetylneuraminate anhydrate, comprising adding or adding dropwise a solvent selected from the group consisting of alcohols and ketones to an aqueous N-acetylneuraminic acid solution containing an ammonium-containing compound and having a pH of 3.0 to 9.0 to precipitate a crystal of ammonium N-acetylneuraminate anhydrate, and collecting the crystal of ammonium N-acetylneuraminate anhydrate from the aqueous solution, can be provided.

6 Claims, 2 Drawing Sheets

CRYSTAL OF AMMONIUM N-ACETYLNEURAMINATE ANHYDRATE, AND PROCESS FOR PRODUCING SAME

CROSS-REFERENCE TO RELATED APPLICATIONS

This patent application is the U.S. national phase of International Patent Application No. PCT/JP2016/052311, filed Jan. 27, 2016, which claims the benefit of Japanese Patent Application No. 2015-014541, filed on Jan. 28, 2015, which are incorporated by reference in their entireties herein.

TECHNICAL FIELD

The present invention relates to a crystal of ammonium N-acetylneuraminate anhydrate, which is useful, for example, as a product, a raw material, an intermediate, or the like of health food, pharmaceuticals, cosmetics, and the like, and a production process thereof.

BACKGROUND ART

N-Acetylneuraminic acid (hereinafter, referred to as NeuAc) is a kind of acidic amino sugar generically called sialic acid and is widely used as a raw material of pharmaceuticals such as an anti-influenza drug, or as a component of food, cosmetics and cell culture media.

NeuAc can be produced by a fermentation method, an enzyme method, an extraction method from a natural product, a chemical synthesis method, or the like. As the known NeuAc crystal, crystals of a dihydrate (Non-Patent Document 1) and an anhydrate (Non-Patent Document 2) are known, but a solution of such a crystal shows strong acidity, and the degree of solubility thereof is relatively low of about 100 g/L at normal temperature. Furthermore, there is a problem with storage stability, for example, the crystal and a solution thereof are gradually discolored to dark brown.

On the other hand, as to the crystal of an ammonium salt of NeuAc, a crystal of monohydrate is known (Patent Document 1). This crystal has a problem with stability under high temperature conditions because of its low melting point near 105° C.

Under such circumstances, a crystal of an ammonium salt of NeuAc, having high storage stability at normal temperature as well as under high temperature conditions, is demanded.

RELATED ART

Patent Document

Patent Document 1: JP-A-61-68418

Non-Patent Document

Non-Patent Document 1: Acta Crystallographica Section B: Structural Crystallography and Crystal Chemistry (1973), 29, pp. 1881-1886
Non-Patent Document 2: Chemistry Letters (1984), 6, pp. 1003-1006

SUMMARY OF THE INVENTION

Problems that the Invention is to Solve

An object of the present invention is to provide a crystal of an ammonium salt of NeuAc, having high storage stability at normal temperature as well as under high temperature conditions, and provide a production process thereof.

Means for Solving the Problems

The present invention relates to following (1) to (6).
(1) A crystal of NeuAc ammonium salt anhydrate.
(2) The crystal described in (1) above, wherein the crystal has peaks at diffraction angles (2θ) of 12.3±0.2°, preferably ±0.1°, 13.7±0.2°, preferably ±0.1°, 14.2±0.2°, preferably ±0.1°, 22.4±0.2°, preferably ±0.1°, and 22.6±0.2°, preferably ±0.1° in powder X-ray diffraction.
(3) The crystal described in (2) above, wherein the crystal further has peaks at diffraction angles (2θ) of 17.1±0.2°, preferably ±0.1°, 21.2±0.2°, preferably ±0.1°, 21.6±0.2°, preferably ±0.1°, 23.5±0.2°, preferably ±0.1°, and 24.8±0.2°, preferably ±0.1° in powder X-ray diffraction.
(4) The crystal described in (3) above, wherein the crystal further has peaks at diffraction angles (2θ) of 27.7±0.2°, preferably ±0.1°, 28.1±0.2°, preferably ±0.1°, 28.4±0.2°, preferably ±0.1°, 28.6±0.2°, preferably ±0.1°, and 42.3±0.2°, preferably ±0.1° in powder X-ray diffraction.
(5) A process for producing a crystal of NeuAc ammonium salt anhydrate, comprising adding or adding dropwise a solvent selected from the group consisting of alcohols and ketones to an aqueous NeuAc solution containing an ammonium-containing compound and having a pH of 3.0 to 9.0 to precipitate a crystal of NeuAc ammonium salt anhydrate, and collecting the crystal of NeuAc ammonium salt anhydrate from the aqueous solution.
(6) The production process described in (5) above, wherein the solvent selected from the group consisting of alcohols and ketones is a solvent selected from C1-C6 alcohols, acetone, methyl ethyl ketone, and diethyl ketone.

Effects of the Invention

According to the present invention, a crystal of NeuAc ammonium salt anhydrate, having high storage stability at normal temperature as well as under high temperature conditions, and production process thereof are provided.

EMBODIMENTS FOR CARRYING OUT THE INVENTION

1. Crystal of NeuAc Ammonium Salt Anhydrate of the Present Invention

The present invention relates to a crystal of NeuAc ammonium salt anhydrate.

Whether the crystal of NeuAc is a crystal of an anhydrate can be confirmed from the fact that the water content as measured using the Karl-Fisher method described later in Analysis Examples is 1.0 wt % or less, preferably 0.95 wt % or less, most preferably 0.9 wt % or less.

Whether the crystal of NeuAc is a crystal of an ammonium salt can be confirmed by measuring the content of ammonium ions contained in the crystal using the HPLC method described later in Analysis Examples.

For example, whether the crystal of NeuAc anhydrate is a crystal of a monoammonium salt can be confirmed from the fact that the ammonium content in the crystal is 5.2±1.0 wt %, preferably 5.2±0.5 wt %, most preferably 5.2±0.3 wt %.

Figure 1:
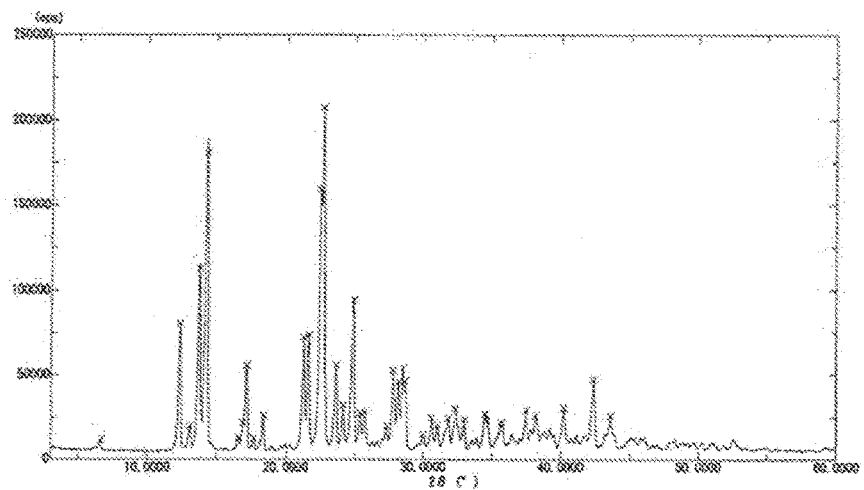
FIG. 1 Illustrating the results of powder X-ray diffraction of the crystal of NeuAc ammonium salt anhydrate obtained in Example 1.
Figure 2:
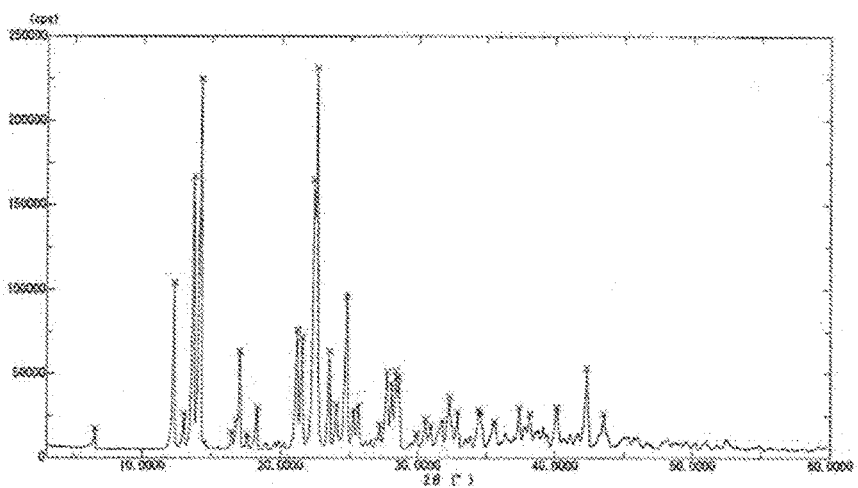
FIG. 2 Illustrating the results of powder X-ray diffraction of the crystal of NeuAc ammonium salt anhydrate obtained in Example 2.
Figure 3:
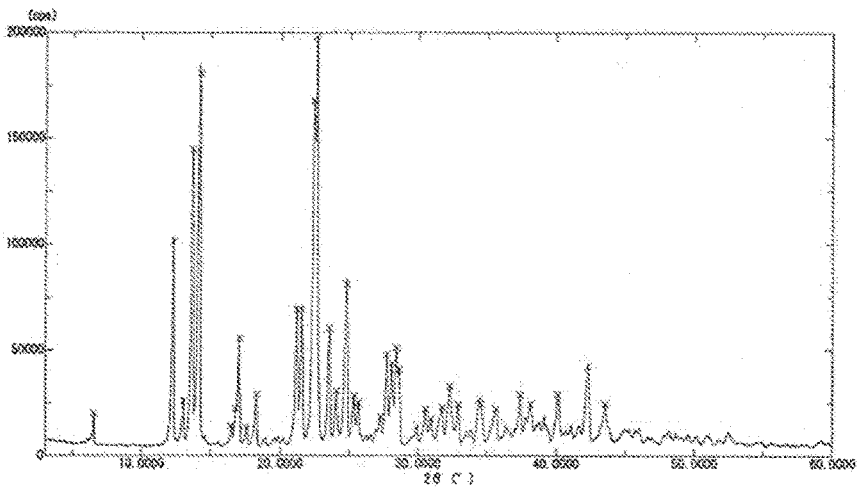
FIG. 3 Illustrating the results of powder X-ray diffraction of the crystal of NeuAc ammonium salt anhydrate obtained in Example 3.

The crystal of the present invention includes a crystal of NeuAc ammonium salt anhydrate whose powder X-ray diffraction pattern using CuKα as the X-ray source is defined by the values shown in FIGS. 1 to 3 and Tables 1, 3, and 6. Here, FIGS. 1, 2 and 3 correspond to the diffraction results of crystals of NeuAc ammonium salt anhydrate of Tables 1, 3, and 6, respectively.

Figure 4:
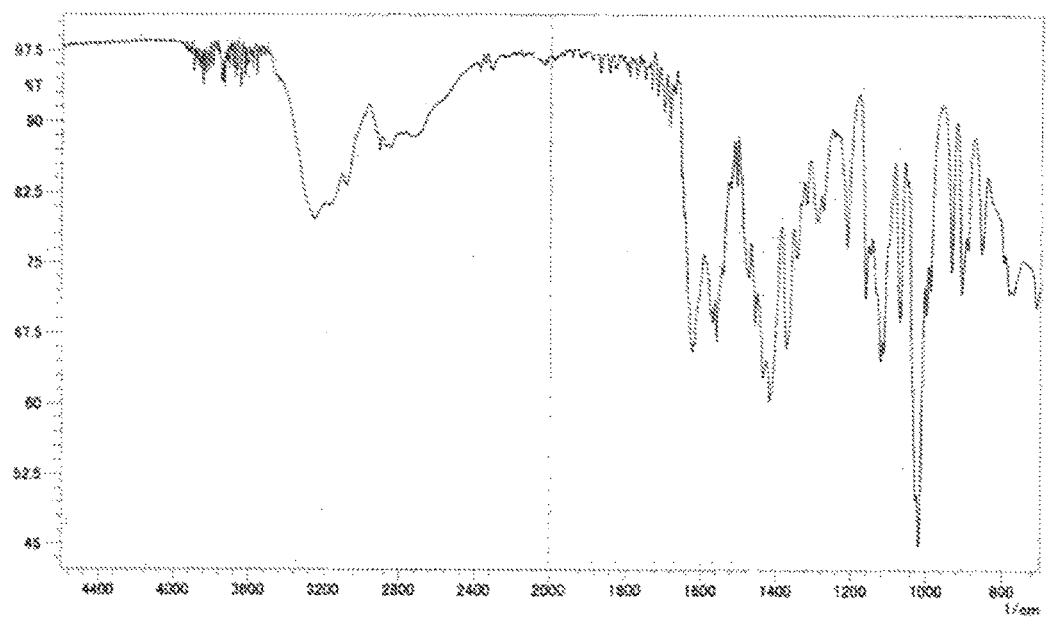
FIG. 4 Illustrating the results of infrared spectroscopic (IR) analysis of the crystal of NeuAc ammonium salt anhydrate obtained in Example 1.

Further, the crystal of the present invention includes a crystal of NeuAc ammonium salt anhydrate showing the infrared absorption spectrum illustrated in FIG. 4 when subjected to the infrared spectroscopic (IR) analysis described later in Analysis Examples.

2. Process for Producing Crystal of NeuAc Ammonium Salt Anhydrate of the Present Invention The process for producing the crystal of NeuAc ammonium salt anhydrate of the present invention is a process comprising adding or adding dropwise a solvent selected from the group consisting of alcohols and ketones to an aqueous NeuAc solution containing an ammonium-containing compound and having a pH of 3.0 to 9.0, preferably 4.5 to 8.5, most preferably 5.5 to 8.0, to precipitate a crystal of NeuAc ammonium salt anhydrate, and collecting the crystal of NeuAc ammonium salt anhydrate from the aqueous solution.

NeuAc contained in the aqueous NeuAc solution may be produced by any of a fermentation method, an enzyme method, an extraction method from a natural product, a chemical synthesis method and other production methods.

In the case where a solid material that obstructs crystallization is contained in the aqueous NeuAc solution, the solid material can be removed using centrifugal separation, filtration, a ceramic filter, or the like. In the case where a water-soluble impurity or salt that obstructs crystallization is contained in the aqueous NeuAc solution, the water-soluble impurity or salt can be removed by passing the aqueous solution through a column packed with an ion exchange resin, or the like.

The concentration of NeuAc in the aqueous solution is 200 g/L or more, preferably 300 g/L or more, more preferably 400 g/L or more, still more preferably 500 g/L or more, most preferably 600 g/L or more. In order to adjust the concentration in the aqueous solution to the concentration above, the aqueous solution can be concentrated by a general concentration method such as a heating concentration method or a vacuum concentration method.

The ammonium-containing compound includes basic compounds such as an aqueous ammonia solution and ammonia gas, and neutral salts such as carbonates of ammonium, sulfates of ammonium, nitrates of ammonium, and chlorides of ammonium. Examples of the neutral salts include ammonium carbonate, ammonium sulfate, ammonium nitrate, and ammonium chloride.

In the case where a basic compound is used as the ammonium-containing compound, an aqueous NeuAc solution containing an ammonium-containing compound and having a pH of 3.0 to 9.0, preferably 4.5 to 8.5, most preferably 5.5 to 8.0, can be obtained by adjusting the pH of the aqueous NeuAc solution using the basic compound.

Alcohols may be C1-C6 alcohols, more preferably C1-C3 alcohols, still more preferably alcohols selected from the group consisting of methanol, ethanol, n-propanol and isopropyl alcohol, most preferably alcohols selected from the group consisting of methanol and ethanol.

Ketones may be ketones selected from acetone, methyl ethyl ketone, and diethyl ketone, preferably acetone.

The temperature of the aqueous solution at the time of adding or adding dropwise a solvent selected from the group consisting of alcohols and ketones may be any temperature as long as NeuAc is not decomposed, but in order to decrease the degree of solubility and thereby enhance the crystallization rate of the crystal of NeuAc ammonium salt anhydrate, the temperature may be 80° C. or less, preferably 70° C. or less, more preferably 60° C. or less, most preferably 50° C. or less.

The amount of the solvent selected from the group consisting of alcohols and ketones to be added or added dropwise may be from 1 to 10 times, preferably from 2 to 8 times, most preferably from 3 to 6 times the amount of the aqueous solution.

The time for which the solvent selected from the group consisting of alcohols and ketones is added or added dropwise may be from 1 to 48 hours, preferably from 3 to 30 hours, most preferably from 5 to 20 hours.

In the step of adding or adding dropwise the solvent selected from the group consisting of alcohols and ketones, before precipitation of a crystal of NeuAc ammonium salt anhydrate, a crystal of NeuAc ammonium salt anhydrate may be added as a seed crystal so that the concentration in the aqueous solution is from 0.2 to 25 g/L, preferably from 0.5 to 10 g/L, most preferably from 2 to 5 g/L.

The time at which the seed crystal is added may be within 1 to 5 hours, preferably within 1 to 4 hours, most preferably within 1 to 3 hours, after dropwise addition or addition of the solvent selected from the group consisting of alcohols and ketones is started.

After a crystal of NeuAc ammonium salt anhydrate is precipitated as described above, the precipitated crystal may be further matured for 1 to 48 hours, preferably for 1 to 24 hours, most preferably for 1 to 12 hours.

The word "mature" means to grow the crystal by once stopping the step of adding or adding dropwise the solvent selected from the group consisting of alcohols and ketones.

After the crystal is matured, the step of adding or adding dropwise the solvent selected from the group consisting of alcohols and ketones may be restarted.

The method for collecting the crystal of NeuAc ammonium salt anhydrate is not particularly limited but may include pressure filtration, suction filtration, centrifugal separation, and the like. Furthermore, in order to reduce the adhesion of the mother liquid and thereby improve the quality of the crystal, the crystal may be appropriately washed. The solution used for crystal washing is not particularly limited, but water, methanol, ethanol, acetone, n-propanol, isopropyl alcohol, and a solution prepared by mixing one kind or a plurality of kinds of members selected from these at an arbitrary ratio may be used.

The thus obtained wet crystal is dried, whereby a final product can be obtained. As for the drying conditions, any method may be used as long as the form of NeuAc ammonium salt anhydrate can be maintained, and reduced-pressure drying, fluidized bed drying, forced air drying, and the like may be applied. The drying temperature may be any temperature as long as the adhered water can be removed, but the temperature may be preferably 80° C. or less, more preferably 60° C. or less.

By employing the above-described crystallization conditions, a high-purity crystal of NeuAc ammonium salt anhydrate can be obtained. The purity of the crystal of NeuAc ammonium salt anhydrate may be 97% or more, preferably 98% or more, more preferably 99% or more, most preferably 99.5% or more.

The crystal of NeuAc ammonium salt anhydrate, which can be produced by the production process above, includes, for example, a crystal of NeuAc ammonium salt anhydrate whose powder X-ray diffraction pattern using CuKα as the X-ray source is defined by the values shown in FIGS. 1 to 3 and Tables 1, 4, and 6.

ANALYSIS EXAMPLES (1) Powder X-Ray Diffraction

The measurement was performed using a powder X-ray diffraction apparatus (XRD), Ultima IV (manufactured by Rigaku Corporation), according to the instruction book.

(2) Measurement of Degree of Solubility

A crystal of NeuAc ammonium salt anhydrate, or a crystal of known NeuAc dihydrate was added to water adjusted to the respective temperatures until each crystal remained undissolved and after keeping the solution for a sufficient time under stirring, the supernatant containing no crystal was collected, and the concentration of NeuAc therein was measured using the following HPLC conditions.

Guard column: Shodex SUGAR SH-G ϕ6.0×50 mm
Column: SUGAR SH1011 ϕ8.0×300 mm×2 columns in series
Column temperature: 60° C.
Buffer: an aqueous 0.005 mol/L sulfuric acid solution
Flow rate: 0.6 mL/min
Detector: UV detector (wavelength: 210 nm)

(3) Measurement of Water Content of Crystal by Karl-Fisher Method

The measurement was performed using an automatic water content measuring device AQV-2200 (manufactured by Hiranuma Sangyo Co., Ltd.) according to the instruction book.

(4) Measurement of Ammonium Content

A crystal of NeuAc ammonium salt anhydrate was dissolved in water, and the concentration of ammonium ions contained in the crystal was measured using the following HPLC conditions.

Column: YMC-Pack ODS-AQ ϕ6.0×150 mm
Column temperature: 40° C.
Buffer: Trisodium citrate dihydrate (14.7 g), anhydrous sodium sulfate (7.1 g), sodium lauryl sulfate (15 g), and 1-propanol (600 mL) are dissolved in deionized water, and the final volume is made up to 5 L, and the pH is adjusted to 3.8 using sulfuric acid.
Reaction solution: Boric acid (18.5 g), sodium hydroxide (10.7 g), N-acetylcysteine (4.6 g), o-phthalaldehyde (0.6 g), and Brij-35 (4.1 mL) are dissolved in deionized water, and the final volume is made up to 1 L.
Flow rate: 1.2 mL/min (mobile phase), 0.4 mL/min (reaction solution)
Detector: excitation wavelength: 355 nm, fluorescence wavelength: 455 nm (5) Measurement of Melting Point The measurement was performed using Melting Point M-565 (manufactured by BUCHI) according to the instruction book.

(6) Infrared Spectroscopic (IR) Analysis

The measurement was performed using Model FTIR-8400 (manufactured by Shimadzu Corporation) according to the instruction book.

Reference Example 1

Acquisition of Noncrystalline Amorphous NeuAc Ammonium Salt

A crystal of NeuAc anhydrate (519.4 g) was dissolved in water, and the pH was adjusted to 6.80 using ammonia water, whereby a NeuAc ammonium salt-containing aqueous solution (650 mL) was prepared. A portion of this aqueous solution was freeze-dried, whereby a white powder was obtained. The powder X-ray diffraction of the powder was measured, and as a result, an X-ray diffraction peak was not confirmed. Therefore, it was found that the powder is in a noncrystalline amorphous state.

Examples are described below, but the present invention is not limited to the following Examples.

Example 1

Acquisition of Crystal of NeuAc Ammonium Salt Anhydrate (1)

NeuAc (1,546.7 g in terms of an anhydrate) was dissolved in water, and the pH was adjusted to 7.67 using ammonia water, and the final volume was made up to 3,800 mL. This aqueous solution was concentrated to 1,800 mL, and a 500 mL portion of the obtained concentrated solution was used for the next step.

While maintaining the 500 mL portion of the concentrated solution at 45° C., 1,500 mL (3 times the amount) of methanol was added dropwise thereto over 3 hours, and then, 400 mL of acetone was added thereto. After maturation for 1 hour, 1,100 mL (final addition amount: 3 times the amount) of acetone was additionally added thereto over 3 hours to precipitate a crystal. The crystal slurry was cooled to 5° C. and matured for 3 hours, and the crystal was then collected by filtration, washed with an aqueous 80% methanol solution and dried under reduced pressure at 25° C., whereby 430.8 g of the crystal was obtained.

The results of powder X-ray diffraction of the crystal are shown in Table 1. In the Table, "2θ" indicates the diffraction angle (2θ°), and "Relative Intensity" indicates the relative intensity ratio ($I/I_0$). The results when the relative intensity ratio was 5 or more are shown.

TABLE 1

| 2θ | Relative Intensity |
|---|---|
| 6.6 | 6 |
| 12.4 | 39 |
| 13.1 | 10 |
| 13.8 | 55 |
| 14.3 | 88 |
| 16.6 | 7 |
| 16.9 | 11 |
| 17.1 | 27 |
| 17.6 | 7 |
| 18.4 | 13 |

TABLE 1-continued

| 2θ | Relative Intensity |
|---|---|
| 21.3 | 35 |
| 21.6 | 36 |
| 22.5 | 77 |
| 22.7 | 100 |
| 23.6 | 27 |
| 24.1 | 16 |
| 24.9 | 46 |
| 25.4 | 14 |
| 25.7 | 14 |
| 27.3 | 10 |
| 27.8 | 26 |
| 28.2 | 23 |
| 28.5 | 26 |
| 28.7 | 23 |
| 30.0 | 7 |
| 30.6 | 12 |
| 31.0 | 10 |
| 31.8 | 12 |
| 32.3 | 15 |
| 33.0 | 12 |
| 34.5 | 14 |
| 34.7 | 12 |
| 35.7 | 11 |
| 37.5 | 15 |
| 38.2 | 13 |
| 40.2 | 15 |
| 42.4 | 23 |
| 43.6 | 13 |

The ammonium content of the crystal as measured by the HPLC method was 5.3 wt % and substantially coincided with the theoretical value (5.2 wt %) of a monoammonium salt. In addition, the amount of water contained in the crystal was 1.0 wt % or less.

From these results, it was found that the crystal is a crystal of NeuAc ammonium salt anhydrate.

Various physical properties of the crystal are shown in Table 2. As for the pH, an aqueous solution at 100 g/L in terms of NeuAc ammonium salt was measured.

TABLE 2

| Water Content % | Ammonium Content % | Melting Point ° C. | pH |
|---|---|---|---|
| 0.95 | 5.3 | 166.2 | 7.07 |

Figure 5:
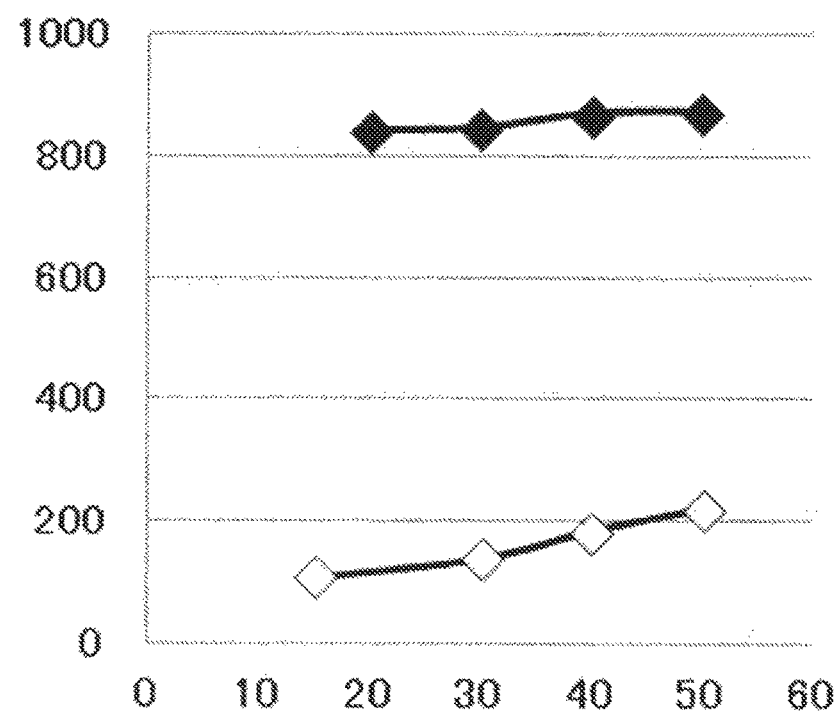
FIG. 5 Illustrating the degrees of solubility of the crystal of NeuAc ammonium salt anhydrate obtained in Example 1 and a crystal of known NeuAc dihydrate; the vertical axis indicates the concentration (g/L) of NeuAc in terms of an anhydrate and the horizontal axis indicates the temperature (° C.).

The degrees of solubility in water of the crystal of NeuAc ammonium salt anhydrate obtained above and a crystal of NeuAc dihydrate are illustrated in FIG. 5.

It was revealed that the crystal of NeuAc ammonium salt anhydrate has a large degree of solubility compared with the degree of solubility of the crystal of known NeuAc dihydrate and has excellent solubility.

In addition, the melting point of the crystal of NeuAc ammonium salt anhydrate is 166.2° C. and is higher than the melting point of around 105° C. of known NeuAc ammonium salt monohydrate salt. Therefore, it was revealed that the crystal of NeuAc ammonium salt anhydrate is stable even under high temperature conditions.

Example 2

Acquisition of Crystal of NeuAc Ammonium Salt Anhydrate (2)

NeuAc (1,475.8 g in terms of an anhydrate) was dissolved in water, and the pH was adjusted to 6.81 using ammonia water, and the final volume was made up to 4,000 mL. This aqueous solution was concentrated to 1,810 mL, and a 40 mL portion of the obtained concentrated solution was used for the next step.

To the 40 mL portion of the concentrated solution, 10 mL of water was added to make the volume up to 50 mL. While maintaining the 50 mL of the solution at 40° C., 40 mL of ethanol was added dropwise thereto over 1 hour. The crystal obtained in Example 1 was added thereto as a seed crystal to precipitate a crystal. After the crystal was matured over 9 hours, 110 mL (final addition amount: 3 times the amount) of ethanol was further added dropwise thereto over 8 hours. The crystal slurry was cooled to 10° C. and matured for 3 hours, and the crystal was then collected by filtration, washed with an aqueous 80% ethanol solution and dried under reduced pressure at 25° C., whereby 32.9 g of the crystal was obtained.

The results of powder X-ray diffraction of the crystal are shown in Table 3. In the Table, "2θ" indicates the diffraction angle (2θ°), and "Relative Intensity" indicates the relative intensity ratio ($I/I_0$). The results when the relative intensity ratio was 5 or more are shown.

TABLE 3

| 2θ | Relative Intensity |
|---|---|
| 6.5 | 8 |
| 12.3 | 46 |
| 13.0 | 12 |
| 13.7 | 73 |
| 14.2 | 98 |
| 16.5 | 7 |
| 16.8 | 10 |
| 17.1 | 28 |
| 17.6 | 6 |
| 18.3 | 13 |
| 21.2 | 33 |
| 21.6 | 31 |
| 22.4 | 72 |
| 22.6 | 100 |
| 23.5 | 28 |
| 24.0 | 14 |
| 24.8 | 42 |
| 25.3 | 13 |
| 25.6 | 14 |
| 27.2 | 9 |
| 27.7 | 22 |
| 28.1 | 20 |
| 28.4 | 23 |
| 28.6 | 21 |
| 29.9 | 7 |
| 30.5 | 10 |
| 30.9 | 9 |
| 31.8 | 10 |
| 32.3 | 16 |
| 32.9 | 12 |
| 34.4 | 13 |
| 34.5 | 12 |
| 35.6 | 10 |
| 37.4 | 13 |
| 38.2 | 12 |
| 40.1 | 13 |
| 42.3 | 24 |
| 43.5 | 12 |

The powder X-ray diffraction pattern and physical properties of the crystal were substantially the same as those of the crystal of NeuAc ammonium salt anhydrate obtained in Example 1, and therefore, it was found that the crystal is also a crystal of NeuAc ammonium salt anhydrate.

Various physical properties of the crystal are shown in Table 4. As for the pH, an aqueous solution at 100 g/L in terms of NeuAc ammonium salt was measured.

TABLE 4

| Water Content % | Ammonium Content % | Melting Point °C. | pH |
|---|---|---|---|
| 0.67 | 5.3 | 168.7 | 6.60 |

With respect to the crystal of NeuAc ammonium salt anhydrate and the noncrystalline amorphous NeuAc ammonium salt acquired in Reference Example 1, the weight change under an atmosphere of 25° C. and a humidity of 60% was compared, and the results are shown in Table 5.

TABLE 5

| Elapsed Time [h] | 0 | 3 | 7 | 24 |
|---|---|---|---|---|
| Crystal of ammonium salt | 0.00 | −0.08 | −0.10 | −0.06 |
| Noncrystalline amorphous | 0.00 | 6.58 | 10.4 | 13.5 |

(Rate of weight change [%])

The noncrystalline amorphous NeuAc ammonium salt exhibited a marked weight increase due to moisture absorption and deliquesced when 24 hours had passed. On the other hand, in the crystal of NeuAc ammonium salt anhydrate, a weight increase was not observed, and therefore, it was revealed that moisture absorption can be suppressed by crystallization.

Example 3

Acquisition of Crystal of NeuAc Ammonium Salt Anhydrate (3)

While maintaining 50 mL of the concentrated solution adjusted in Example 2 at 40° C., 25 mL (0.5 times the amount) of methanol was added dropwise thereto over 1 hour. A seed crystal was added thereto and the crystal was matured for 4 hours, and then, 225 mL (final addition amount: 5 times the amount) of methanol was added dropwise thereto over 12 hours to precipitate a crystal. The crystal slurry was cooled to 10° C. and matured for 3 hours, and then, the crystal was collected by filtration, washed with an aqueous 80% methanol solution and dried under reduced pressure at 25° C., whereby 40.6 g of a crystal was obtained.

The results of powder X-ray diffraction of the crystal are shown in Table 6. In the Table, "2θ" indicates the diffraction angle (2θ°), and "Relative Intensity" indicates the relative intensity ratio ($I/I_0$). The results when the relative intensity ratio was 5 or more are shown.

TABLE 6

| 2θ | Relative Intensity |
|---|---|
| 6.5 | 11 |
| 12.3 | 52 |
| 13.0 | 14 |
| 13.7 | 74 |
| 14.2 | 92 |
| 16.5 | 8 |
| 16.8 | 12 |
| 17.0 | 28 |
| 17.6 | 7 |
| 18.3 | 15 |
| 21.2 | 36 |
| 21.6 | 36 |
| 22.4 | 85 |
| 22.6 | 100 |
| 23.5 | 31 |

TABLE 6-continued

| 2θ | Relative Intensity |
|---|---|
| 24.0 | 16 |
| 24.8 | 41 |
| 25.3 | 15 |
| 25.6 | 13 |
| 27.2 | 10 |
| 27.7 | 25 |
| 28.1 | 23 |
| 28.4 | 26 |
| 28.6 | 21 |
| 29.9 | 8 |
| 30.5 | 12 |
| 30.9 | 9 |
| 31.7 | 12 |
| 32.3 | 17 |
| 32.9 | 13 |
| 34.4 | 14 |
| 34.6 | 13 |
| 35.6 | 12 |
| 37.4 | 15 |
| 38.1 | 13 |
| 40.1 | 15 |
| 42.3 | 22 |
| 43.5 | 13 |

The powder X-ray diffraction pattern of the crystal was substantially the same as those of the crystals of NeuAc ammonium salt anhydrates obtained in Examples 1 and 2, and therefore, it was found that the crystal is also a crystal of NeuAc ammonium salt anhydrate.

Various physical properties of the crystal are shown in Table 7. As for the pH, an aqueous solution at 100 g/L in terms of NeuAc ammonium salt was measured.

TABLE 7

| Water Content % | Ammonium Content % | Melting Point °C. | pH |
|---|---|---|---|
| 0.60 | 5.2 | 167.5 | 6.39 |

With respect to the crystal of NeuAc ammonium salt anhydrate and a crystal of known NeuAc dihydrate, the degree of coloration when stored in a closed system at 60° C. was compared, and the results are shown in Table 8. The degree of coloration is expressed by transmittance T % 430 nm=$100 \times 10^{-A}$ (A=Abs: 430 nm, 1 cm), which was obtained by dissolving each crystal at 100 g/L in terms of an anhydrate and performing measurement for the solution.

TABLE 8

| Elapsed Time [days] | 0 | 3 | 6 |
|---|---|---|---|
| Crystal of ammonium salt | 99.73 | 98.87 | 98.49 |
| Dihydrate crystal | 100.1 | 73.26 | 50.46 |

(Transmittance T % 430 nm)

It was found that the coloration of the crystal of NeuAc ammonium salt anhydrate during storage is extremely low compared with the crystal of known NeuAc dihydrate.

INDUSTRIAL APPLICABILITY

According to the present invention, a crystal of NeuAc ammonium salt anhydrate, which is useful, for example, as a product, a raw material, an intermediate, or the like of health food, pharmaceuticals, cosmetics, and the like, and a production process thereof are provided.

DESCRIPTION OF REFERENCE NUMERALS AND SIGNS

In FIG. 5, the black diamond indicates the crystal of NeuAc ammonium salt anhydrate, and the white diamond indicates the crystal of NeuAc dihydrate.

The invention claimed is:

1. A crystal of ammonium N-acetylneuraminate anhydrate.

2. The crystal according to claim 1, wherein the crystal has peaks at diffraction angles (2θ) of 12.3±0.2°, 13.7±0.2°, 14.2±0.2°, 22.4±0.2°, and 22.6±0.2° in powder X-ray diffraction.

3. The crystal according to claim 2, wherein the crystal further has peaks at diffraction angles (2θ) of 17.1±0.2°, 21.2±0.2°, 21.6±0.2°, 23.5±0.2°, and 24.8±0.2° in powder X-ray diffraction.

4. The crystal according to claim 3, wherein the crystal further has peaks at diffraction angles (2θ) of 27.7±0.2°, 28.1±0.2°, 28.4±0.2°, 28.6±0.2°, and 42.3±0.2° in powder X-ray diffraction.

5. A process for producing a crystal of ammonium N-acetylneuraminate anhydrate, comprising adding or adding dropwise a solvent selected from the group consisting of alcohols and ketones to an aqueous N-acetylneuraminic acid solution containing an ammonium-containing compound and having a pH of 3.0 to 9.0 to precipitate a crystal of ammonium N-acetylneuraminate anhydrate, and collecting the crystal of ammonium N-acetylneuraminate anhydrate from the aqueous solution.

6. The production process according to claim 5, wherein the solvent selected from the group consisting of alcohols and ketones is a solvent selected from C1-C6 alcohols, acetone, methyl ethyl ketone, and diethyl ketone.

* * * * *